United States Patent [19]

Xu

[11] Patent Number: 6,083,921

[45] Date of Patent: Jul. 4, 2000

[54] PHARMACEUTICAL COMPOSITIONS AND METHOD OF USING SAME

[76] Inventor: Kai Jian Xu, 826 S. Bell, Garden Apt., Chicago, Ill. 60612

[21] Appl. No.: 09/005,934

[22] Filed: Jan. 12, 1998

[51] Int. Cl.[7] .......................... A61K 31/56; A61K 31/70; A61K 35/78; C07H 1/08

[52] U.S. Cl. .......................... 514/25; 514/28; 424/195.1; 536/8; 536/128; 549/403

[58] Field of Search ................... 424/195.1; 549/403; 514/28, 25; 536/8, 128

[56] References Cited

U.S. PATENT DOCUMENTS

| | | | |
|---|---|---|---|
| 2,224,807 | 12/1940 | Bockmühl et al. | 536/8 |
| 2,425,291 | 8/1947 | Wilson | 536/8 |
| 2,727,890 | 12/1955 | Wender et al. | 536/8 |
| 3,700,775 | 10/1972 | Turbanti | 514/557 |
| 4,124,724 | 11/1978 | Agoro | 514/570 |
| 4,212,799 | 7/1980 | Nuzzolo et al. | 530/377 |
| 4,269,857 | 5/1981 | Tokuda et al. | 424/325 |
| 4,352,792 | 10/1982 | Ishitsuka et al. | 424/180 |
| 4,465,673 | 8/1984 | Tanaka et al. | 424/180 |
| 4,469,685 | 9/1984 | Kojima et al. | 424/195.1 |
| 4,859,769 | 8/1989 | Karlsson et al. | 536/53 |
| 4,872,987 | 10/1989 | Kopsch et al. | 210/635 |
| 5,178,865 | 1/1993 | Ho et al. | 424/195.1 |
| 5,411,733 | 5/1995 | Hozumi et al. | 424/195.1 |
| 5,478,579 | 12/1995 | Sawruk | 424/535 |

FOREIGN PATENT DOCUMENTS

| | | |
|---|---|---|
| 1089848A | 7/1994 | China . |
| 1090185 | 8/1994 | China . |
| 0348509 | 1/1990 | European Pat. Off. ....... A61K 31/12 |
| 60-243016 | 12/1985 | Japan . |
| 04018019 | 1/1992 | Japan . |
| WO 92/07842 | 5/1992 | WIPO .......................... C07D 305/14 |
| WO 9725054 | 8/1997 | WIPO . |

OTHER PUBLICATIONS

Derwent Abstract, AN 97–458038 c43!; XP–002101773; PN CN111.7851.A 960306; Abstract only. (Mar. 1996).

Derwent Abstract, AN 86–018 507 c25!; XP–002101774; PN JP60243016 A; Abstract only. (Dec. 1985).

Wleklik et al., Interferon–Inducing Activity of Flavonoids, *ACTA Microbiologica Polonica*, vol. 36, No. 1 2, pp. 151–154 (1987).

Fieser et al., *Chemistry*, 2 Ed., pp. 877–881 (1950), no month found.

Wang Yue–hong et al., *Clinical and Experimental Study on Treatment of Acute Respiratory Tract Infection with Shuanghuanglian Aerosol*, CJIM, 2(3)2: 162–165 (1996), no month found.

Xu et al., Human Bioavailability of the Injection and the Aerosol of "Shuang Huang Lian", *Pharmaceuticals*, 11:417 (1993), no month found.

Merraim–Webster's Collegiate Dictionary, tenth edition, p. 19. Merriam–Webster, Inc. Springfield, MA (1996). No month given.

Derwent abstract AN 97–133214. Hua et al., patent # CN 1089848. (Jul. 27, 1994).

Wleklik et al., Acta Microbiol. Pol. 36(1–2), pp. 151–154. Abstract only. (1987). No month found.

Nishibi et al., Chaem. Pharm. Bull. 30(3), pp. 1048–1050. (1982). No month found.

Nagai et al., Antiviral Research. 19, pp. 207–217. (1992). No month found.

Kubo et al. Planta Medica. 43, pp. 194–201. (1981). No month found.

*Primary Examiner*—Ralph Gitomer
*Assistant Examiner*—Marjorie A. Moran
*Attorney, Agent, or Firm*—Leydig, Voit & Mayer, Ltd.

[57] ABSTRACT

The present invention provides a pharmaceutical composition comprising an extract or combination of extracts having an antiviral, antibacterial, or immunomodulating property, wherein the extract or combination of extracts is obtained from a combination of plants wherein at least one plant is selected from each of the genuses Labiatae, Caprifoliaceae, and Oleaceae. A preferred extract is obtained from *Radix scutellaria*, *Flos lonicera*, and *Fructus forsythiae*. The present invention further provides a pharmaceutical composition comprising baicalin, chlorogenic acid and forsythiaside in isolated and purified form. The present invention further provides certain novel derivatives of baicalin, chlorogenic acid and forsythiaside. The present invention additionally provides processes for preparing the extracts as well as baicalin, chlorogenic acid, and forsythiaside in isolated and purified forms.

11 Claims, No Drawings

PHARMACEUTICAL COMPOSITIONS AND METHOD OF USING SAME

TECHNICAL FIELD OF THE INVENTION

The present invention relates to pharmaceutical compositions having anitiviral, antibacterial, or immunomodulating property in general, and in particular to pharmaceutical compositions useful in the treatment or prevention of infection by a parainfluenza or respiratory syncytial virus.

BACKGROUND OF THE INVENTION

The pharmaceutical industry has been developing for many years medicines for the treatment of viral or bacterial infections such as the common cold, flu, and bronchitis. Natural and synthetic products have been considered as possible candidates for these drugs. See, for example, U.S. Pat. No. 4,352,792, which discloses certain 3-alkoxyflavones reportedly useful in treating mammals having infections caused by the human rhinoviruses, enteroviruses and influenzaviruses. U.S. Pat. No. 4,465,673 discloses that 1,2,3,6-pentagalloylglucose is effective against certain viruses, for example, herpes simplex virus. Wang et al. (CJIM, 2(3), 162–165 (1996)) states that a certain formulation called Shuanghuanglian (SHL) is useful for the treatment of acute respiratory tract infection. Wang et al. merely states that the "recipe of SHL consists of Flos lonicerae, Radix scutellariae and Fructus fosythiae" and fails to provide a teaching that would allow those skilled in the art to prepare SHL.

Although there are many drugs, over the counter as well as prescription, available to the public, there is a continuing need for drugs which are effective against these diseases without causing significant side effects.

These and other objects and advantages of the present invention, as well as additional inventive features, will be apparent from the description of the invention provided herein.

SUMMARY OF THE INVENTION

The foregoing needs have been fulfilled to a great extent by the present invention which provides a pharmaceutical composition comprising an extract or combination of extracts having an antiviral, antibacterial, or immunomodulating property, wherein the extract or the combination of extracts is obtained from a combination of plants, wherein the combination of plants includes at least one plant from each of the genuses Labiatae, Caprifoliaceae, and Oleaceae.

The present invention also provides a pharmaceutical composition comprising an extract or a combination of extracts having an antiviral, antibacterial, or immunomodulating property, wherein the extract or combination of extracts is obtained from a combination of *Radix scutellariae*, *Flos lonicerae* and *Fructus Forsythiae*. This extract is referred to herein as the RFF extract.

The present invention further provides a pharmaceutical composition having an antiviral, antibacterial, or immunomodulating property, comprising baicalin, chlorogenic acid, and forsythiaside, particularly in isolated and purified form.

The present invention further provides a compound of the formula I or II:

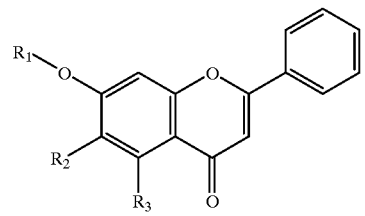

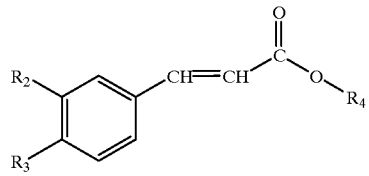

wherein $R_1$ is a sugar residue having 4–6 carbon atoms, optionally having a substituent selected from the group consisting of COOH and an amide, ester, and salt thereof, cyano, amino, substituted amino, alkyl, hydroxyalkyl, halo, and nitro; $R_2$ and $R_3$ are selected from the group consisting of hydroxy, alkyloxy, alkyl carbonyl, alkyl carbonyloxy, alkyloxy carbonyl, halo, cyano, nitro, and amino; wherein one or more aromatic hydrogens may be replaced with a substituent selected from the group consisting of hydroxy, cyano, amino, substituted amino, alkyl, hydroxyalkyl, halo, and nitro; and wherein $R_4$ is a cyclohexyl or disaccharide moiety optionally substituted with one or more substituents selected from the group consisting of COOH and an amide, ester, and salt thereof, cyano, amino, alkyl amino, alkyl, alkyloxy, hydroxyalkyl, hydroxy, halo, nitro, aryl, alkyl aryl, and aryl alkyl wherein said aryl group may be further substituted with one or more substituents selected from the group consisting of COOH and an amide, ester, and salt thereof, cyano, amino, alkyl amino, alkyl, hydroxyalkyl, hydroxy, alkyloxy, halo, and nitro, with the proviso that the compound is not baicalin, chlorogenic acid or fosythiaside.

The present invention further provides a pharmaceutical composition comprising a pharmaceutically acceptable carrier and a compound of formula I or II.

The present invention further provides a method of treating or preventing a viral or bacterial infection or enhancing the immune response in a mammal comprising administering to the mammal a pharmaceutical composition of the present invention.

The present invention further provides a process for preparing the RFF extract comprising the steps of:

(1) preparing an extract of *Radix scutellariae*, which comprises the steps of:

(a) extracting *Radix scutellariae* with water at a temperature above about 25° C. to provide a first extract;

(b) concentrating the first extract to provide a concentrate having a relative density of from about 1.20 to about 1.25 at 80° C.;

(c) adjusting the pH of the concentrate to a level of from about 1 to about 2 at 80° C.;

(d) cooling the concentrate to produce a precipitate and recovering the precipitate;

(e) mixing the precipitate with water to obtain a paste;

(f) adjusting the pH of the paste to about 7;

(g) dissolving the paste in ethanol to obtain a first ethanolic solution; and optionally filtering the solution to remove any suspended impurities; and (h) concentrating the first ethanolic solution to obtain an extract of Radix scutellariae having a relative density less than about 1.03 at 40° C.; and (2) preparing a combined extract of *Flos lonicerae* and *Fructus Forsythiae* which comprises the steps of:

(a) extracting a mixture of *Flos lonicerae* and *Fructus forsythiae* with water at a temperature above about 25° C. to provide a second extract;

(b) concentrating the second extract to provide a second concentrate having a relative density of from about 1.20 to about 1.25 at 80° C.;

(c) cooling the second concentrate to about 40° C.;

(d) adding ethanol to the second concentrate to obtain a second ethanolic solution and removing any precipitate from the solution;

(e) concentrating the second ethanolic solution to remove the ethanol and recovering the combined extract of *Flos lonicerae* and *Fructus Forsythiae;* and (3) combining the extract of *Radix scutellariae* and the combined extract of *Flos lonicerae* and *Fructus forsythiae* to obtain the RFF extract.

The present invention further provides a process for isolating baicalin in a purified form from a plant material containing baicalin comprising:

(a) contacting the plant material with water at an elevated temperature to produce a water extract;

(b) recovering the water extract;

(c) adjusting the pH of the water extract to an acidic pH;

(d) diluting the extract with water to obtain a precipitate;

(e) dissolving the precipitate in an aqueous alkali solution to obtain a neutral solution of the precipitate;

(f) diluting the neutral solution with an alcohol to obtain an alcoholic solution;

(g) adjusting the pH of the alcoholic solution to an acidic pH and obtaining a precipitate containing baicalin; and (h) recovering the purified baicalin.

The present invention further provides a process for isolating chlorogenic acid in a purified form from a plant material containing chlorogenic acid comprising:

(a) contacting the plant material with water to obtain a water extract;

(b) partitioning the water extract with an organic solvent to obtain an organic phase containing chlorogenic acid;

(c) concentrating the organic phase to obtain a concentrate;

(d) purifying the concentrate on a chromatographic column; and (e) recovering the purified chlorogenic acid.

The present invention further provides a process for isolating forsythiaside in a purified form from a plant material containing forsythiaside comprising:

(a) contacting the plant material with water at an elevated temperature to obtain a water extract;

(b) concentrating the water extract to obtain a concentrate;

(c) contacting the extract with an organic solvent to obtain an organic solution;

(d) recovering and concentrating the organic solution to obtain a residue containing forsythiaside;

(e) purifying the residue on a chromatographic column; and (f) recovering the purified forsythiaside.

While the invention has been described and disclosed below in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

The present invention provides a pharmaceutical composition comprising an extract or combination of extracts having an antiviral, antibacterial, or immunomodulating property. The extract or combination of extracts is obtained from a combination of plants wherein the combination of plants includes at least one plant from each of the genuses Labiatae, Caprifoliaceae, and Oleaceae.

Any suitable subgenus or species of these plant genuses can be used to obtain the extracts or combination of extracts for the inventive pharmaceutical composition. A particular example of a suitable subgenus of Labiatae is Scutellaria L., a particular example of a suitable subgenus of Caprifoliaceae is Lonicera L., and a particular example of a suitable subgenus of Oleacea is a Forsythia V. Any suitable species can be used. A preferred Scutellaria L. specie is *Scutellaria baicalensis* Georgi, a preferred Lonicera L. specie is Lonicerae Japonica (Thunb.), and a preferred Forsythia V. specie is *Forsythia suspensa* (Thunb.) Vahl. Thus, a preferred extract is obtained from a combination of plants that includes *Scutellaria baicalensis* Georgi, Lonicera Japonica (Thunb.), and Forsythia suspensa (Thunb.) Vahl.

Any suitable part of the plant can be used. For example, leaves, twigs, branches, bark, roots, flowers, and fruits can be used.

A description of the above plant species follows. *Scutellaria baicalensis* Georgi is a perennial herbaceous plant with robust and cone-shaped root, quadrigonal stem, 30–60 cm high opposite leaf, terminal panicle, labiate corolla, and purpureous, with a fluorescence time of from July to August and a bearing time of from August to September. This plant grows in the Hebei, Shanxi, and Heilongjiang provinces of the People's Republic of China (PRC). A preferred part of the plant is the root, also known as *Radix scutellariae.*

*Lonicera japonica* Thunb. is a semi-evergreen vine with dark red young branch papery leaf, ovate 3–5 cm long corolla white, yellow late, 3–4.5 cm long, labiate, with a fluorescence time of from April to June and a bearing time of from October to November. This plant grows in the Shandong and Henan provinces of PRC. A preferred part of the plant is the flower, also known as *Flos Lonicera.*

*Forsythia suspensa* (Thunb.) Vahl is a deciduous vine with 2–4 m high branch spreading or extended with a little trailing monophyllous, opposite leaf, flower blossoms before leaf shows, axillary about 2.6 cm long capsule narrow ovate 1.5 cm long, with a fluorescence time of from March to May and a bearing time of from July to August. This plant grows in the Shanxi, Henan, and Shandong provinces of PRC. A preferred part of the plant is the fruit, also known as *Fructus Forsythiae.*

An extract containing the combined extracts of *Radix scutellariae* (R), *Flos Lonicera* (F) and *Fructus forsythiae* (F), RFF, is particularly preferred. The RFF extract possesses antiviral, antibacterial, and immunostimulating properties.

The present invention further provides a process for preparing an RFF extract. The RFF extract can be prepared by any suitable method. For example, an extract can be prepared from each plant and a combined RFF extract can be prepared by suitably combining the extracts from the other plants. A preferred process is set forth below. The process comprises the steps of:

(1) preparing an extract of *Radix scutellariae,* which comprises the steps of:

(a) extracting *Radix scutellariae* with water at a temperature above about 25° C. to provide a first extract;

(b) concentrating the first extract to provide a concentrate having a relative density of from about 1.20 to about 1.25 at 80° C.;

(c) adjusting the pH of the concentrate to a level of from about 1 to about 2 at 80° C.;

(d) cooling the concentrate to produce a precipitate and recovering the precipitate;

(e) mixing the precipitate with water to obtain a paste;

(f) adjusting the pH of the paste to about 7;

(g) dissolving the paste in ethanol to obtain a first ethanolic solution; and optionally filtering the solution to remove any suspended impurities; and (h) concentrating the first ethanolic solution to obtain an extract of *Radix scutellariae* having a relative density less than about 1.03 at 40° C.; and (2) preparing a combined extract *Flos lonicerae* and *Fructus Forsythiae* which comprises the steps of:

(a) extracting a mixture of *Flos lonicerae* and *Fructus Forsythiae* with water at a temperature above about 25° C. to provide an extract;

(b) concentrating the second extract to provide a second concentrate having a relative density of from about 1.20 to about 1.25 at 80° C.;

(c) cooling the second concentrate to about 40° C.;

(d) adding ethanol to the second concentrate to obtain a second ethanolic solution and removing any precipitate from the solution;

(e) concentrating the second ethanolic solution to remove the ethanol and recovering the combined extract of *Flos lonicerae* and *Fructus Forsythiae* and (3) combining the extract of *Radix scutellariae* and the combined extract of *Flos Lonicerae* and *Fructus forsythiae* to obtain the RFF extract.

Any suitable alcohol, preferably ethanol, can be used in the above process.

The RFF extract can have any suitable combination of the three plant parts. For example, the plant parts R:F:F can be in the ratio of about 0.5–1:0.5–1:1–2, preferably about 1:1:2.

The present invention further provides a pharmaceutical composition comprising baicalin, chlorogenic acid, and forsythiaside, particularly in isolated and purified form. The present inventor has carried out painstaking and extensive research to identify the active ingredients in the plant extracts. Particularly, it has been discovered by the present inventor that baicalin isolated from the Scutellaria plant, *Scutellaria baicalensis* Georgi, is effective as a component of the pharmaceutical composition of the present invention.

Further, it has been discovered by the present inventor that chlorogenic acid is an important ingredient of the plant extract of *Lonicera japonica* (Thunb.) and is effective as a component of the pharmaceutical composition of the present invention.

In addition, it has been discovered by the present inventor that forsythiaside is an important ingredient of the plant extract of *Forsythia suspensa* (Thunb.) Vahl and is effective as a component of the pharmaceutical composition of the present invention. The formulas of baicalin, chlorogenic acid, and forsythiaside are set forth herein below:

Baicalin 5,6-Dihyroxy-4-oxo-2-phenyl-4H-t-benzopyran-7-yl-β-D-glucopyranosiduronic acid

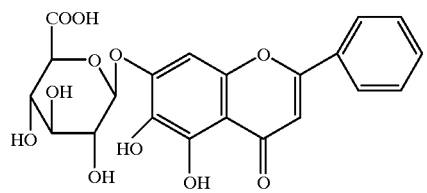

Chlorogenic acid 3-(3-(3,4-dihydroxyphenyl)-[-oxo-2-propenyl]oxy)-1,4,5-trihydroxy-,[1S-(1a,3b, 4a, 5a)]-cyclohexanecarboxylic acid

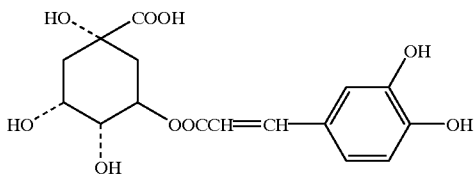

Forsythiaside (3,4-dihydroxy-β-phenothyl-O-α-L-rhamno-pyranosyl-(1→6)-4-O-caffeoyl-β-D-glucopyranoside)

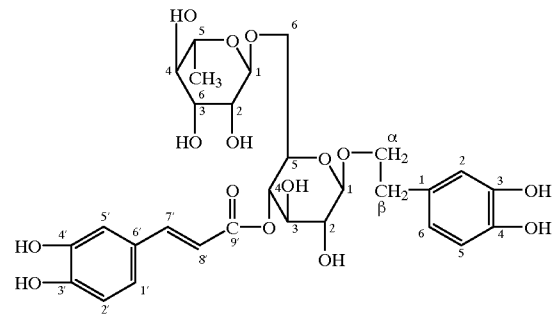

The present invention further provides an antiviral, antibacterial, or immunostimulating composition comprising the active ingredients baicalin (B), chlorogenic acid (C), and forsythiaside (F). This composition is referred to herein as the BCF composition. The BCF composition, by virtue of its greater purity of the active ingredients, is as equally as effective as the RFF composition at lower concentrations of the ingredients. Thus, smaller concentrations of the active ingredients can be used in BCF. Any possible side effect is minimized because of the greater purity of the ingredients and the reduced concentration of the ingredients.

The present invention further provides a process for isolating baicalin in a purified form from a plant material containing baicalin comprising:

(a) contacting the plant material with water at an elevated temperature to produce a water extract;

(b) recovering the water extract;

(c) adjusting the pH of the water extract to an acidic pH;

(d) diluting the extract with water to obtain a precipitate;

(e) dissolving the precipitate in an aqueous alkali solution to obtain a neutral solution of the precipitate;

(f) diluting the neutral solution with an alcohol to obtain an alcoholic solution;

(g) adjusting the pH of the alcoholic solution to an acidic pH and obtaining a precipitate containing baicalin; and (h) recovering purified baicalin.

Any suitable organic solvent, preferably an alcohol, more preferably ethanol, can be used in the above process.

Thus, for example baicalin preferably is isoloated in purified form from *Radix Scutellarie* as follows: The plant part is cut into small pieces and extracted with water at an elevated temperature, for example, at a temperature of from about 60° C. to about 100° C., and preferably at about 90° C. The ratio of water-to-plant weight is selected such that water is in excess, preferably about 8 times that of the plant. The extraction can be repeated to insure high recovery of the active ingredient. The extracts are combined to yield a combined extract, which can be filtered to remove any suspended impurities.

The filtered extract is then acidified, for example, with conc. HCl, to a pH of about 2. The acidified extract is diluted with excess water to obtain a precipitate, which is then separated from the supernatant, e.g., by filtration. The filtered precipitate then is mixed with an aqueous alkali solution, e.g., a 20% by wt. NaOH solution and the resulting neutral solution is mixed with an organic solvent, preferably ethanol. The resulting ethanol solution is then acidified, e.g., with HCl to a pH of about 2 to obtain baicalin as a precipitate. The precipitate is then dried at about 80° C. for about 4 hours to obtain baicalin in isolated and purified form.

The present invention further provides a process for isolating chlorogenic acid in a purified form from a plant material containing chlorogenic acid comprising:

(a) contacting the plant material with water to obtain a water extract;

(b) partitioning the water extract with an organic solvent to obtain an organic phase containing chlorogenic acid;

(c) concentrating the organic phase to obtain a concentrate;

(d) purifying the concentrate on a chromatographic column; and (e) recovering chlorogenic acid.

Any suitable organic solvent, preferably an alcohol, and more preferably n-butanol, can be used in the above process.

Thus, for example, chlorogenic acid preferably is isolated in purified form from *Flos lonicerae* as follows: The plant part is extracted by stirring with excess water, preferably at a 10-fold excess, for about an hour. The water extract is separated from the residue which is contacted with fresh excess water to yield a second extract. The combined extract is filtered to remove any suspended impurities. The extract is concentrated to reduce the volume by a factor of about 2, and the concentrated extract is then extracted with an organic solvent, e.g., n-butanol. After the solvent removal, the solids subjected to a further purification on a chromatographic column, preferably on a polyamide column. The adsorbed product is eluted using a 30% ethanol solution. The ethanol solvent is then recovered on a HPLC column, e.g., a $C_{18}$ column. Chlorogenic acid that is retained in the column is eluted using a methanol-water (2:3 v/v) eluant. The solvent is removed from the eluate, e.g., by freeze drying, to recover purified chlorogenic acid.

The present invention further provides a process for isolating forsythiaside in a purified form from a plant material containing forsythiaside comprising:

(a) contacting the plant material with water at an elevated temperature to obtain a water extract;

(b) concentrating the water extract to obtain a concentrate;

(c) contacting the extract with an organic solvent to obtain an organic solution;

(d) recovering and concentrating the organic solution to obtain a residue containing forsythiaside;

(e) purifying the residue on a chromatographic column; and (f) recovering purified forsythiaside.

Any suitable organic solvent, preferably an alcohol and more preferably methanol, can be used in the above process.

Thus, for example, forsythiaside preferably is isolated in purified form from *Fructus forsythiae* as follows: The plant part is extracted with water at an elevated temperature, preferably at about 100° C. The water extract is separated from the residue. The residue is extracted again with water at an elevated temperature, and the extract is collected. The combined extract is filtered to remove any insoluble impurities and then concentrated to reduce the volume. The concentrated extract is extracted with a hot organic solvent, e.g., methanol. The organic phase is separated and the solvent is removed to yield a residue which is then subjected to chromatographic purification on a silica gel column using chloroform-methanol (5:1 v/v) gradient as the eluant. The eluate is concentrated on a HPLC column, e.g., on a $C_{18}$ column. Forsythiaside adsorbed on the column is eluted using methanol-water (1:1 v/v) to obtain an eluate containing purified forsythiaside. The eluate is concentrated and freeze-dried to obtain forsythiaside in isolated and purified form.

The pharmaceutical compositions of the present invention are particularly suitable for treating or preventing an infection by bacteria and other viruses that affect the respiratory system. Particular examples of these viruses include parainfluenza virus types 1, 2, 3, and 4, and respiratory syncytial virus (RSV) of the long type.

The pharmaceutical compositions of the present invention are particularly suitable for treating or preventing infection by bacteria selected from the group consisting of *Vibrio metchnikovii, Edwardsiella tarda, Proteous vulgaris, Shigalla flexneri, Shigalla sonnei, Staphylococcus aureus, Proteus mirabilis, Citrobacter freundil,* Group D *streptococcus, P. shigelloides, Aeromonas hydrophilia, Salmonella typhi, Pseudomonas aeruginosa, E. coli, H. alvei, Enterobacter cloacea, Staphylococcus epidermis, Streptococcus pneumoniae,* Branhamella, and *Bacillus subtilis.*

The pharmaceutical compositions of the present invention are further capable of enhancing the natural killer (NK) cell activity or augmenting the production of interferon-alpha.

The present invention further provides a method of treating or preventing a viral or bacterial infection in a mammal comprising administering to said mammal a pharmaceutical composition as described above.

The present invention further provides a method of enhancing the NK cell activity or augmenting the production of interferon-alpha of a mammal comprising administering to the mammal a pharmaceutical composition described above.

The present invention further provides a compound of the formula I or II:

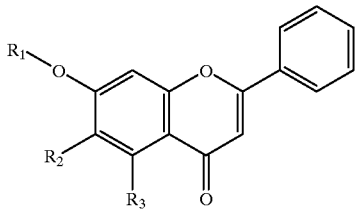

(I)

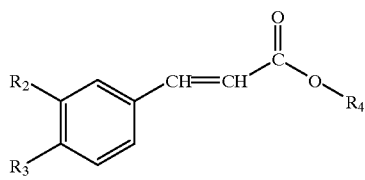

(II)

wherein $R_1$ is a sugar residue having 4–6 carbon atoms optionally having a substituent selected from the group consisting of COOH and an amide, ester, and salt thereof, cyano, amino, substituted amino, alkyl, hydroxyalkyl, halo, and nitro; $R_2$ and $R_3$ are selected from the group consisting of hydroxy, alkyloxy, alkyl carbonyl, alkyl carbonyloxy, alkyloxy carbonyl, halo, cyano, nitro, and amino; wherein one or more aromatic hydrogens may be replaced with a substituent selected from the group consisting of hydroxy, cyano, amino, substituted amino, alkyl, hydroxyalkyl, halo, and nitro; and wherein $R_4$ is a cyclohexyl or disaccharide moiety, optionally substituted with one or more substituents selected from the group consisting of COOH and an amide, ester, and salt thereof, cyano, amino, alkyl amino, alkyl, alkyloxy, hydroxyalkyl, hydroxy, halo, nitro, aryl, alkyl aryl, and aryl alkyl, wherein said aryl group may be further substituted with one or more substituents selected from the group consisting of COOH and an amide, ester, and salt thereof, cyano, amino, alkyl amino, alkyl, hydroxyalkyl, hydroxy, alkyloxy, halo, and nitro, with the proviso that the compound is not baicalin, chlorogenic acid or fosythiaside.

Preferred examples of the above compounds include those wherein $R_2$ and $R_3$ are hydroxy. Preferred examples of the compounds include those wherein aryl alkyl is phenylethyl. Preferred examples of the compounds of the present invention include those wherein $R_4$ is cyclohexyl substituted with 1–3 hydroxyl groups and a carboxyl. A further preferred $R_4$ is a cyclohexyl substituted with 3 hydroxyl groups and a carboxyl. Other preferred examples of the compounds of the present invention include those wherein $R_4$ is a disaccharide, particularly a rhamnopyranosyl glucopyranoside. A further preferred disaccharide is 3,4-dihydroxy-β-phenothyl-O-L-rhamnopyranosyl-(1→6)-β-D-glucopyranoside.

The term "sugar" herein refers to any suitable sugar moiety known to those of ordinary skill in the art including mono and disaccharide moieties. Preferred sugar moieties include monosaccharides having 4–6 carbon atoms. Hexoses are particularly preferred. Glucose is a preferred hexose. A glucose moiety having a carboxyl is further preferred. A preferred $R_1$ is β-D-glucopyranosiduronic acid.

The term "alkyl" herein refers to an alkyl moiety of any suitable chain length. Preferred alkyl moieties include those having 1–6 carbon atoms. The term "aryl" herein refers to aromatic groups having 1–3 rings, preferably a phenyl.

The compounds of formula I and II can be prepared by methods known to those of ordinary skill in the art. For example, these compounds can be prepared by suitable modification of baicalin, chlorogenic acid, or forsythiaside. Thus, for example, a hydroxyl group can be converted to an ether by converting the hydroxyl to alkoxide followed by the reaction of the alkoxide with an alkyl iodide. The aromatic ring hydrogens can be replaced by substituents such as nitro, e.g., by an electrophilic substitution reaction. An amino group can be obtained by the reduction of the nitro group, e.g., by platinum/hydrogen. The aromatic ring positions can be halogenated, e.g., photochemically. An alkyl group can be introduced into the aromatic ring via Friedel-Craft alkylation procedures known to those of ordinary skill in the art. A carboxyl group can be introduced in the sugar moiety by oxidation, e.g., of the hydroxymethyl group. A carboxyl group can be converted to the amide by reaction with an amine, followed by dehydration. A carboxyl group can be converted to the ester by reaction with an alcohol under acidic conditions. Other derivatives can also be prepared by methods known to those of ordinary skill in the art including those disclosed in common text books; see, e.g., *Advanced Organic Chemistry*, J. March, $3^d$ Ed. (1985).

The present invention further provides a pharmaceutical composition comprising a pharmaceutically acceptable carrier and an effective (e.g., therapeutically or prophylactically effective) amount of at least one of the compounds set forth above.

The present invention further provides a method of treating or preventing a viral or bacterial infection in a mammal comprising administering to the mammal an effective amount (e.g., therapeutically or prophylactically effective) of at least one of the compounds set forth above.

The present invention further provides a method of enhancing the NK cell activity or augmenting the production of interferon-alpha of a mammal comprising administering to the mammal at least one of the compounds set forth above.

The pharmaceutically acceptable carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See, *Pharmaceutics and Pharmacy Practice,* J.B. Lippincott Co., Philadelphia, Pa., Banker and Chalmers, eds., pages 238–250 (1982), and *ASHP Handbook on Injectable Drugs,* Toissel, 4th ed., pages 622–630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. The dosages range from about 0.001 to about 1000 mg/kg body weight of the animal being treated/day. Preferred dosages range from about 0.01 to about 10 mg/kg body weight/day, and further preferred dosages range from about 0.01 to about 1 mg/kg body weight/day.

The following examples further illustrate the present invention but, of course, should not be construed as in any way limiting its scope.

EXAMPLE 1

This example illustrates the preparation of the RFF extract. The RFF extract was prepared by combining the extract of *Radix scutellariae* and the combined extract of *Flos Lonicera* and *Fructus fosythiae*. The materials used and the method of preparation are set forth below.

The extract of *Radix scutellariae* was prepared as follows:

The plant part (500 g) was cut into small slices, and sufficient water was added to cover the slices. The combination was heated, and the water was allowed to boil for 2 hours. The water extract was separated and saved. Sufficient amount of water again was added to cover the residue slices, and the water was allowed to boil for 1 hour. The second extract also was saved. The residue was extracted with boiling water once more to obtain a third extract.

The three extracts were combined and concentrated by boiling until the relative density of the liquid was in the range of 1.20–1.25 at 80° C. The pH of the resulting liquid was adjusted to 1.0–2.0 with HCl (2 mol/L) at 80° C. The liquid was stored at 80° C. for 1 hour and then allowed to sit at room temperature for 24 hours. The supernatant solution was discarded, and a small amount of water was added to the residue which was then beaten to form a paste. The pH of the paste was adjusted to 7.0 with 40% NaOH, and an equal volume of 95% ethanol was added to the mixture. The mixture was stirred until the reconstituted residue dissolved. The resulting solution was filtered. The solution was then concentrated to have a relative density of no less than 1.03 at 40° C. This solution was allowed to cool to room temperature. This is the extract of *Radix scutellariae*.

The combined extract of *Flos lonicerae* and *Fructus Forsythiae* was prepared as follows:

*Flos lonicerae* (500 g) and *Fructus forsythiae* (1000 g) were bathed in warm water for 30 minutes, and then the bath water was boiled for 1.5 hours. The water extract was separated and saved. The residue was boiled again in water for 1.5 hours. The extract was saved. The two extracts were combined and concentrated by boiling to attain a solution of relative density of 1.20–1.25 at 80° C. The solution was cooled to 40° C., and ethanol was added gradually and with stirring to attain a concentration of 75% ethanol. The mixture was allowed to stand for 24 hours and then filtered to remove the precipitate. The precipitate was rinsed with 75% ethanol and filtered. All the filtered liquids were combined, and the ethanol was removed until the residual liquid was free of ethanol odor. The residual liquid was mixed with ethanol to attain a concentration of 85% ethanol. The mixture was allowed to stand for 24 hours and filtered. The precipitate was rinsed with 85% ethanol and filtered. All the filtered liquids were combined, and the ethanol was recovered from the filtered liquid until ethanol odor could not be detected in the extract.

The extract of *Radix scutellariae* prepared earlier was combined with the extract prepared above, and the combination was concentrated by boiling to 2000 ml.

EXAMPLE 2

This example illustrates the virostatic and bacteriostatic activity as well as the immunomodulating effects of the pharmaceutical compositions of the present invention. One embodiment of the present invention, RFF, is a composition comprising an extract of a mixture of *Radix scutellariae, Flos lonicerae, Fructus forsythiae*. Another embodiment of the present invention is BCF which is a mixture of the active ingredients of the above three plants, i.e., a mixture of baicalin, chlorogenic acid and forsythiaside. The materials used, the method of testing, and the results obtained are discussed below:

Materials and Methods

1. Pharmaceutical Compositions

RFF—each ml contained an extract from a mixture containing 0.25 g Radix scutellariae, 0.25 g *Flos lonicerae* and 0.5 g *Fructus forsythiae*.

BCF—each ml contained 2 mg baicalin, 1 mg chlorogenic acid and 1 mg forsythiaside. Cell maintenance media were used as control.

2. Cell Types

K562, Wsh, Hela, and Hep-2 cells were employed in this study. The cells were maintained and passaged under conditions known to those skilled in the art.

3. Viruses

The following viruses were tested: parainfluenza virus types: 1, 2, 3, and 4; and respiratory syncytial virus of the long type.

These viruses were obtained from the China Institute of Medical Sciences Laboratory and were maintained according to established protocols known to those skilled in the art. Their TCD50 and agglutination titers were determined by published methods.

4. Bacterial Strains

The bacterial strains tested are set forth in Table 1. These strains were obtained from the China Institute of Medical Sciences and maintained according to established protocols.

5. NK Cell Activity Assay

To each well of the 96-well plate, 0.1 ml effector cells (containing 5000 lymphocytes) and 0.1 ml target cells (containing 500 K562 cells) were added. Each sample was made in triplicate. The cells were incubated at 37° C., 5% $CO_2$ for 24 hours. The serum was then removed, following which 0.1 ml DNAase (100 mg/ml) and 0.1 ml trypsin (4 mg/ml) were added, and the cells were further incubated for another 24 hours. The cells were then pulsed with $^3$H-thymidine for 4 hours and harvested onto fiber filters, and the amount of $^3$H-thymidine (CPM) on the filter was determined by scintillation counting. The wells that did not have added target cells served as control.

HTdR release %=Target cell (CPM)–control (CPM)

6. Determination of the Activity of Inteferon-Alpha

The tested specimens were serially diluted in duplicate and added to a monolayer of Wsh cells. Normal cells with and without added virus were used as control cells. The specimens were incubated at 37° C. for 24 hours, and then 200TCD50VSV were added. The cells with added virus were then scored when they showed +++ virus induced pathological changes. The results obtained are discussed below.

Results

1. Virostatic Studies

Both BCF and RFF were diluted to 0.5% by wt. concentration with cell maintenance media. Three groups (Groups A–C) of tests were performed.

Group A: The above solutions were added individually to monolayer cells, and the cells were incubated for 2 hours at 37° C. 100TCD50 virus suspensions were added and then removed and replaced with cell maintenance media.

Group B: The above solutions were individually mixed with 100TCD50 virus suspensions incubated at 37° C. for 1 hour and then added to monolayer cells. The cells were kept at 37° C. for 1 hour and then replaced with cell maintenance media.

Group C: After the monolayer cells were exposed to the virus for 24 hours, of either BCF or RFF were added to the cells.

The controls were normal cells exposed to the virus and not to BCF or RFF. All specimens were incubated at 37° C. for 7 days, and then the virus was titered. The compositions were found to have antiviral activity if the viral load between the treatment groups and the control groups was reduced four-fold. The results obtained are set forth in Table 1.

TABLE 1

Antiviral activity of RFF and BCF

| Virus | BCF A | BCF B | BCF C | RFF A | RFF B | RFF C | CONTROL A | CONTROL B | CONTROL C |
|---|---|---|---|---|---|---|---|---|---|
| Parainfl. 1 | − | + | + | − | + | + | − | − | − |
| Parainfl. 2 | − | + | + | − | + | + | − | − | − |
| Parainfl. 3 | − | + | + | − | + | + | − | − | − |
| Parainfl. 4 | − | + | + | − | + | + | − | − | − |
| RSV | − | + | + | − | + | + | − | − | − |

'+' means an antiviral effect was observed, '−' means no antiviral effect was observed. "Parainfl." stands for parainfluenza virus.

The results were obtained in triplicate and were unequivocal. The results demonstrated that RFF and BCF were effective in reducing the virotoxic effects of parainfluenza virus types 1–4 as well as RSV when RFF and BCF were administered with the virus (Group B) or after viral exposure (Group C).

2. Bacteriostatic Studies

A. The bacteria were allowed to grow for 16–24 hours and then the bactererial density was determined by established methods with the final bacterial concentration kept at one billion/ml. The bacteria grew in both liquid and solid media, and bacterial densities were measured after 16–24 hours. The results obtained are set forth in Table 2.

3. Anti-Staph. Aureus Animal Studies

A. Staphylococcus aureus was obtained from the China Institute of Medical Sciences Laboratory. The bacteria were cultured in both blood agar and glucose based media. The MCD towards white mice was determined to be 50 million/animal.

B. Animal experiments were carried out on laboratory bred white mice of average weight 18–22 g. The male and female mice were equal in numbers.

C. Anti-Staphylococcus aureus studies

The pharmaceutical compositions used were BCF or RFF as described above. Concentrations used were as follows: 2 μg/0.1 ml, 4 μg/0.1 ml, 6 μg/0.1 ml, 8 μg/0.1 ml., 10 μg/0.1 ml., 12 μg/0.1 ml, and 14 μg/0.1 ml.

The mice (total n=160) were divided into a BCF group (n=70), RFF group (n=70), and control groups (n=20). There were two control groups with 10 animals serving as positive and negative controls.

Each animal in the BCF group was injected with 50 millions staphylococcus aureus via the tail vein, and the animals were subdivided into seven groups. Each group received a different concentration of BCF, and the medications were given intraperitoneally daily starting 6 hours post staphylococcus aureus injections. Seven days later, the survival rate of the animals was determined. Studies using RFF were performed similarly.

TABLE 2

Antibacterial effect of RFF and BCF

| Bacteria | BCF[1] Concentration (%) 20 | 10 | 5 | 2.5 | RFF[1] Concentration (%) 20 | 10 | 5 | 2.5 | Control[1] Concentration (%) 20 | 10 | 5 | 2.5 |
|---|---|---|---|---|---|---|---|---|---|---|---|---|
| *Serratia marcescens* | + | + | + | + | + | + | + | + | + | + | + | + |
| *Vibrio metchnikovli* | − | − | − | − | − | − | − | + | + | + | + | + |
| *Edwardsiella tarda* | − | − | − | − | − | − | − | + | + | + | + | + |
| *Proteus vulgaris* | − | − | − | + | − | − | − | + | + | + | + | + |
| *Shigalla flexneri* | − | − | + | + | − | − | + | + | + | + | + | + |
| *Staphylococcus aureus* | − | − | − | − | − | − | − | − | + | + | + | + |
| *Proteus mirabilis* | − | − | − | + | − | − | − | + | + | + | + | + |
| *Citrobacter freundil* | − | − | + | + | − | − | + | + | + | + | + | + |
| Group D streptococcus | − | + | + | + | − | + | + | + | + | + | + | + |
| *P. shigelloides* | − | − | − | − | − | − | − | − | + | + | + | + |
| *Aeromonas hydrophilia* | − | − | − | + | − | − | − | + | + | + | + | + |
| *Salmonella typhi* | − | − | + | + | − | − | − | + | + | + | + | + |
| *Pseudomonas aeruginosa* | − | − | + | + | − | − | + | + | + | + | + | + |
| *Escherichia Coli* | − | + | + | + | − | + | + | + | + | + | + | + |
| *H. alvei* | − | + | + | + | − | + | + | + | + | + | + | + |
| *Enterobacter cloacae* | − | − | + | + | − | − | + | + | + | + | + | + |
| *Staphylococcus epidermidis* | − | − | + | − | − | − | + | + | + | + | + | + |
| *Staphylococcus citreus* | + | + | + | + | + | + | + | + | + | + | + | + |
| *Streptococcus pneumoniae* | − | − | + | + | − | − | + | + | + | + | + | + |
| *Enterobacter aerogenes* | + | + | + | + | + | + | + | + | + | + | + | + |
| *Branhamella* | − | − | + | + | − | − | + | + | + | + | + | + |
| *Bacillus subtilis* | − | − | + | + | − | − | + | + | + | + | + | + |

'—' indicates no bacterial growth was observed.
'+' indicates bacterial growth was observed.
[1]The BCF, RFF or control solution was prepared by diluting the original solutions (see Materials and Methods - 1. Pharmaceutical compositions) by a factor of 5, 10, 20, or 40 to obtain 20, 10, 5, or 2.5% BCF, RFF, or control solution, respectively.

The above results demonstrate that each of BCF and RFF had bacteriostatic effect on a number of different bacteria. The effect of each of BCF and RFF correlated with the concentration being used, with the least effect seen at the lowest concentration.

The positive control group consisted of 10 animals receiving the bacteria and normal saline, and the negative control group consisted of 10 animals receiving neither bacteria nor a pharmaceutical composition. The ED50 was determined by the Cou's method. The results obtained are set forth in Tables 3–4.

TABLE 3

Results of Anti-Staphylococcus aureus studies with BCF
BCF

| group | dose (μg/animal) | n | death | mortality rate | logarithm of dose |
|---|---|---|---|---|---|
| 1 | 2 | 10 | 10 | 1.0 | 0.3010 |
| 2 | 4 | 10 | 8 | 0.8 | 0.6021 |
| 3 | 6 | 10 | 6 | 0.6 | 0.7782 |
| 4 | 8 | 10 | 4 | 0.4 | 0.9031 |
| 5 | 10 | 10 | 3 | 0.3 | 1.0 |
| 6 | 12 | 10 | 2 | 0.2 | 1.0792 |
| 7 | 14 | 10 | 0 | 0 | 1.1461 |

The ED50 was calculated to be 6.6621 μg/animal, with 95% confidence level between 5.3215 and 8.5901 μg/animal.

TABLE 4

Results of Anti-Staphylococcus aureus studies with RFF
RFF

| group | dose (μg/animal) | n | death | mortality rate | logarithm of dose |
|---|---|---|---|---|---|
| 1 | 2 | 10 | 10 | 1.0 | 0.301 |
| 2 | 4 | 10 | 8 | 0.8 | 0.602 |
| 3 | 6 | 10 | 6 | 0.6 | 0.778 |
| 4 | 8 | 10 | 5 | 0.5 | 0.903 |
| 5 | 10 | 10 | 3 | 0.3 | 1.0 |
| 6 | 12 | 10 | 2 | 0.2 | 1.0792 |
| 7 | 14 | 10 | 0 | 0 | 1.1461 |

The ED50 was calculated to be 6.747 μg/animal, with a 95% confidence level between 5.2264 and 8.7136 μg/animal.

The positive control group animals receiving only the normal saline all died. The negative control group animals were all alive. The above data demonstrated that both BCF and RFF had antistaphylococus aureus activity.

4. Effect on Peripheral Blood NK Cell Activity

Peripheral blood lymphocytes were obtained from human volunteers and then divided and prepared as follows Group A: Lymphocytes+1640 growth media
Group B: Lymphocytes+1% RFF 1640 growth media
Group C: Lymphocytes+0.5% RFF 1640 growth media
Group D: Lymphocytes+0.256 RFF 1640 growth media The cells were then incubated at 37° C. for 48 hours and the NK cell activity was determined. The results obtained are set forth in Table 5.

TABLE 5

Effect of RFF concentration on NK cell activity

| Group | n | NK activity (X +/− SD) | P value |
|---|---|---|---|
| A | 20 | 46.28 +/− 7.6 | — |
| B | 20 | 66.47 +/− 8.36 | <0.01 |
| C | 20 | 68.11 +/− 9.6 | <0.01 |
| D | 20 | 60.87 +/− 8.2 | <0.01 |

X = mean; SD = standard deviation

Similar studies were performed using BCF and the results obtained were as follows:

TABLE 6

Effect of BCF concentration on NK cell activity

| Group | n | NK activity (X +/− SD) | P value |
|---|---|---|---|
| A | 20 | 47.28 +/− 8.0 | — |
| B | 20 | 68.48 +/− 7.06 | <0.01 |
| C | 20 | 68.44 +/− 9.31 | <0.01 |
| D | 20 | 69.81 +/− 7.5 | <0.01 |

X = mean; SD = standard deviation

The above results demonstrated that 0.24%–1% RFF or BCF was able to enhance NK cell activity.

5. Effect on Peripheral Blood Lymphocytes on the Production of Interferon-Alpha

Peripheral blood lymphocytes were exposed to varying concentrations of RFF or BCF in a growth medium and Newcastle disease virus (NDV). The control lymphocytes were exposed to NDV and growth medium and not to RFF or BCF.

Group A: Peripheral blood lymphocytes+1640 growth media+NDV (virus added control)
Group B: Peripheral blood lymphocytes+1% RFF 1640 growth media+NDV
Group C: Peripheral blood lymphocytes+0.5% RFF 1640 growth media+NDV
Group D: Peripheral blood lymphocytes+0.25% RFF 1640 growth media+NDV The results obtained are set forth in Table 7.

TABLE 7

Effect of RFF on peripheral blood lymphocytes production of interferon-alpha

| Group | n | Interferon-alpha (u/ml, X +/− SD) | t |
|---|---|---|---|
| A | 20 | 4182 +/− 272 | — |
| B | 20 | 7260 +/− 804 | <0.01 |
| C | 20 | 8844 +/− 912 | <0.01 |
| D | 20 | 8680 +/− 863 | <0.01 |

X = mean; SD = standard deviation; u/ml = units/ml

The above results demonstrated that concentrations of 0.25%–1% RFF enhanced the production of interferon-alpha by peripheral blood lymphocytes.

Studies were performed with BCF in a similar manner, and the results obtained are set forth in Table 8.

TABLE 8

Effect of BCF on the production of interferon-alpha by peripheral blood lymphocytes

| Group | n | Interferon-alpha (u/ml, X +/− SD) | t |
|---|---|---|---|
| A | 20 | 4182 +/− 272 | — |
| B | 20 | 7360 +/− 814 | <0.01 |
| C | 20 | 8744 +/− 913 | <0.01 |
| D | 20 | 8686 +/− 843 | <0.01 |

X = mean; SD = standard deviation; u/ml = units/ml

The above results demonstrate that BCF in concentrations ranging from 0.25%–1% enhanced the production of interferon-alpha by peripheral blood lymphocytes.

6. Effect on NK Cell Activity and Production of Interferon—Alpha in Rabbits

Rabbits (total n=60) were divided into a BCF group (n=20), RFF group (n=20) and control group (n=20). In both the BCF and RFF groups, 5 ml of each medication was injected via the neck vein into the rabbits while the control group received 5 ml of normal saline injection. The injections were continued daily for a total of 5 days, and peripheral blood samples were obtained from the animal's neck artery. NK cell activity as well as interferon-alpha concentrations were determined. The results obtained are set forth in Tables 9–10.

TABLE 9

Effect of RFF on NK cell activity and level of interferon - alpha in rabbits

| Group | n | NK cell activity X +/− SD | Inteferon (u/ml, X +/− SD) |
|---|---|---|---|
| RFF | 20 | 60.24 +/− 12.13 | 1536 +/− 134 |
| Control | 20 | 38.92 +/− 8.2 | 724 +/− 92 |
| t | | <0.01 | <0.01 |

X = mean; SD = standard deviation; u/ml = units/ml

TABLE 10

Effect of BCF of NK cell activity and level of interferon-alpha in rabbits

| Group | n | NK cell activity X +/− SD | Inteferon, u/ml, X +/− SD |
|---|---|---|---|
| BCF | 20 | 61.15 +/− 11.14 | 1632 +/− 125 |
| Control | 20 | 38.92 +/− 8.2 | 724 +/− 92 |
| t | | <0.01 | <0.01 |

X = mean; SD = standard deviation; u/ml = units/ml

The above results demonstrate that both BCF and RFF enhanced the activity of NK cell activity as well as the production of interferon-alpha by peripheral blood lymphocytes in rabbits.

The foregoing confirms that RFF and BCF have virostatic effects towards RSV and Parainfluenza virus types 1–4. Both in vitro and in vivo data support that both RFF and BCF have bacteriostatic effects on staphylococcus aureus. In vitro data also show that RFF and BCF were effective against pathogens such as Proteus, Shigalla, Salmonella, Pseudomonas, Enterobacter cloacae, Streptococcus. Both BCF and RFF enhance NK cell activity as well as augment the production of interferon-alpha by peripheral blood lymphocytes. Interferon-alpha is an important cytokine in resisting viral infection. Interferon-alpha also possesses an immunomodulating function. It enhances the activity of NK cell activity, augments the macrophage-like function and directly participates in regulating several biomolecules within the cells. NK cells serve an important immunosurveillence function. They participate directly in eliminating viral infected cells as well as the viral particles itself. NK cells are also important in producing interferon-alpha. These two effects help form an effective immunobarrier in resisting viral related illnesses.

All of the patents and publications cited herein are incorporated in their entirety by reference.

While this invention has been described with an emphasis upon the preferred embodiment, it will be obvious to those of ordinary skill in the art that variations of the preferred embodiment may be used and that it is intended that the invention may be practiced otherwise than as specifically described herein. Accordingly, this invention includes all modifications encompassed within the spirit and scope of the invention as defined by the following claims.

What is claimed is:

1. A pharmaceutical composition comprising a pharmaceutically acceptable carrier, baicalin, chlorogenic acid, and forsythiaside.

2. A method of treating a viral or bacterial infection in a mammal comprising administering to said mammal the pharmaceutical composition of claim 1.

3. A method of enhancing the NK cell activity or augmenting the production of interferon-alpha of a mammal comprising administering to said mammal the pharmaceutical composition of claim 1.

4. An aerosol composition comprising a pharmaceutically acceptable carrier and baicalin, chlorogenic acid, and forsythiaside in isolated and purified form.

5. A method of treating a viral or bacterial infection in a mammal comprising administering to said mammal the aerosol composition according to claim 4.

6. A method of enhancing the NK cell activity or augmenting the production of interferon-alpha of a mammal comprising administering to said mammal the aerosol composition according to claim 4.

7. A process for preparing a purified extract from *Radix scutellariae, Flos lonicerae,* and *Fructus forsythiae,* said extract having antiviral, antibacterial, or immunostimulating activity in a mammal, said process comprising the steps of:

(1) preparing an extract of *Radix scutellariae,* which comprises the steps of:
 (a) extracting *Radix scutellariae* with water at a temperature above about 25° C. to provide a first extract;
 (b) concentrating the first extract to provide a first concentrate having a relative density of from about 1.20 to about 1.25 at 80° C.;
 (c) adjusting the pH of the first concentrate to a level of from about 1 to about 2 at 80° C.;
 (d) cooling the concentrate from step (c) to produce a precipitate and recovering the precipitate;
 (e) mixing the precipitate with water to obtain a paste;
 (f) adjusting the pH of the paste using NaOH to about 7;
 (g) dissolving the paste from step (f) in ethanol to obtain a first ethanolic solution; and optionally filtering the solution to remove any suspended impurities; and
 (h) concentrating the first ethanolic solution to obtain an extract of *Radix scutellariae* having a relative density less than about 1.03 at 40° C.; and (2) preparing a combined extract of *Flos lonicerae* and *Fructus forsythiae* which comprises the steps of:
 (a) extracting a mixture of *Flos lonicerae* and *Fructus forsythiae* with water at a temperature above about 25° C. to provide a second extract and a residue;
 (b) extracting the residue with boiling water to obtain a third extract;
 (c) combining the second and third extracts to provide a fourth extract;
 (d) concentrating the fourth extract to provide a second concentrate having a relative density of from about 1.20 to about 1.25 at 80° C.;
 (e) cooling the second concentrate from step (d) to about 40° C.;
 (f) adding ethanol to the second concentrate from step (e) to obtain a second ethanolic solution having an ethanol concentration of 75% and removing any precipitate from the solution;

(g) concentrating the second ethanolic solution from step (f) to remove the ethanol and recovering a residual liquid;

(h) combining the residual liquid from step (g) with ethanol to obtain a mixture having an ethanol concentration of 85%;

(i) allowing the mixture from step (h) to stand;

(j) filtering the mixture from step (i) to recover a third ethanolic solution; and (k) concentrating the third ethanolic solution from step (i) to obtain the combined extract of *Flos lonicerae* and *Fructus forsythiae;* and (3) combining the extract of *Radix scutellariae* from step (1) and the combined extract of *Flos lonicerae* and *Fructus forsythiae* from step (2) to obtain the purified extract wherein said purified extract is suitable for use in aerosol formulation.

8. A compound of the formula

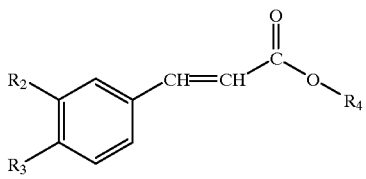

wherein $R_2$ and $R_3$ are selected from the group consisting of hydroxy, alkyloxy, alkyl carbonyl, alkyl carbonyloxy, alkyloxy carbonyl, halo, cyano, nitro, and amino; wherein one or more aromatic hydrogens may be replaced with a substituent selected from the group consisting of hydroxy, cyano, amino, substituted amino, alkyl, hydroxyalkyl, halo, and nitro; and wherein $R_4$ is a disaccharide moiety optionally substituted with one or more substituents selected from the group consisting of COOH and an amide, ester, and salt of the COOH group, cyano, amino, alkyl amino, alkyl, alkyloxy, hydroxyalkyl, hydroxy, halo, nitro, aryl, alkyl aryl, and aryl alkyl wherein said aryl group of aryl, alkyl aryl, and aryl alkyl may be further substituted with one or more substituents selected from the group consisting of COOH and an amide, ester, and salt of the COOH group, cyano, amino, alkyl amino, alkyl, hydroxyalkyl, hydroxy, alkyloxy, halo, and nitro, with the proviso that the compound is not chlorogenic acid or forsythiaside.

9. A pharmaceutical composition comprising a pharmaceutically acceptable carrier and at least one compound of claim 8.

10. A method of treating a viral or bacterial infection in a mammal comprising administering to said mammal at least one compound of claim 8.

11. A method of enhancing the NK cell activity or augmenting the production of interferon-alpha of a mammal comprising administering to said mammal at least one compound of claim 8.

* * * * *